United States Patent [19]

Flynn et al.

[11] Patent Number: 4,747,419

[45] Date of Patent: May 31, 1988

[54] NAIL POLISH COMPOSITIONS AND MEANS FOR APPLYING SAME

[75] Inventors: Madeline D. Flynn, Bridgeport; Alan J. Suares, Cheshire, both of Conn.

[73] Assignee: Chesebrough-Pond's, Inc., Greenwich, Conn.

[21] Appl. No.: 875,184

[22] Filed: Jun. 17, 1986

[51] Int. Cl.⁴ ............................................ A45D 29/00
[52] U.S. Cl. ........................................................ 132/73
[58] Field of Search .......................................... 132/73

[56]  References Cited
U.S. PATENT DOCUMENTS 3,592,202  7/1971  Jones .

FOREIGN PATENT DOCUMENTS 0085370  1/1983  European Pat. Off. .

Primary Examiner—Gregory E. McNeill
Attorney, Agent, or Firm—Brumbaugh, Graves, Donohue & Raymond

[57]  ABSTRACT

The present invention relates to a novel nail polish composition to be dispersed by way of a pen having a substantially non-bristle brush tip; said composition having a low viscosity, i.e. not greater than about 200 cps and comprising a nitrocellulose film former, a relatively high pigment concentration, and an amount of a suitable copolymer of hydrophobic and hydrophilic monomers to aid in preventing said pigment form separating in the tip of the pen.

30 Claims, 1 Drawing Sheet

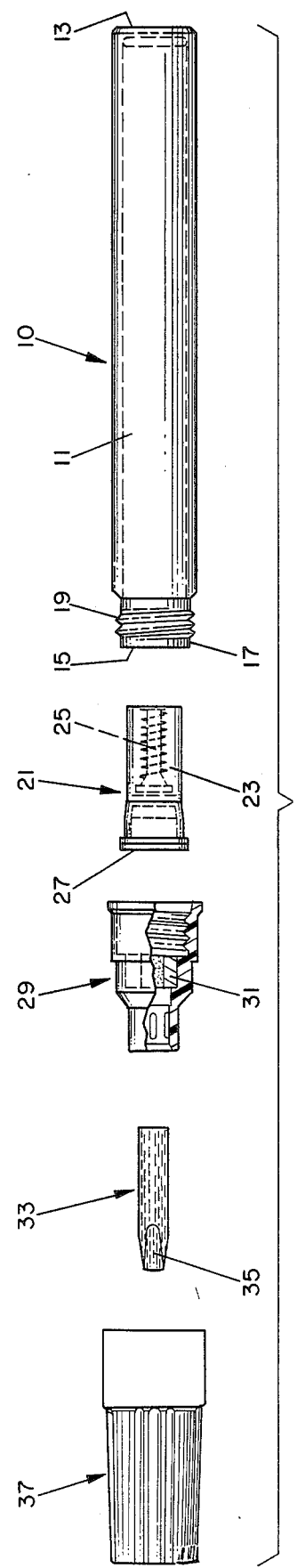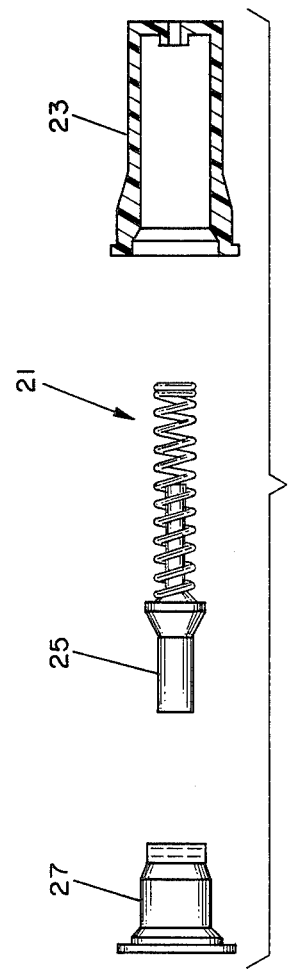

NAIL POLISH COMPOSITIONS AND MEANS FOR APPLYING SAME

SPECIFICATION

The present invention relates to a novel nail polish composition to be dispensed by way of a pen having a substantially non-bristle brush tip. More specifically, the invention is directed to a nail polish formulation having a low viscosity, i.e. not greater than about 200 cps, and comprising a nitrocellulose film former, a relatively high pigment concentration, and a suitable copolymer of hydrophobic and hydrophilic monomers present in an amount sufficient to aid in preventing said pigment from separating in the tip of the pen.

BACKGROUND OF THE INVENTION

Conventionally known nail polish formulations have been used in pen-like applicators of the type disclosed in U.S. Pat. No. 3,592,202. The pen comprises two bristle brush tips, one at each end and two reservoirs, one containing nail polish, the other containing nail polish remover. Nail polish or remover is delivered to the bristle tip of the pen by compressing the reservoir housing containing the fluid formulation. This technique of delivering either polish or remover to the brush is for all practical purposes similar to the technique of dipping a brush into a reservoir of nail polish or remover, insofar as neither technique requires anything other than conventional nail polish or remover formulations in order to effect proper delivery of the polish or remover to the bristle brush tip. Accordingly, said prior art techniques are dependent upon the use of conventional nail polishes, the viscosities of which are sufficiently high enough to enable the polish to be held on the applicator brush.

In contrast to the prior art techniques for applying polish to nail surfaces, the present invention utilizes a substantially non-bristle nib, one end of which contacts a reservoir which is filled with a novel nail polish. When the tip of the nib is depressed polish is released from the reservoir and saturates the nib throughout its entire length, thereby enabling the delivery of a controlled flow of polish to the end of the nib upon contact with the nail surface. Conventional nail polish formulations are unsuitable for use with the applicator means of the present invention, primarily due to their high viscosities, i.e. generally greater than about 300 cps. As used herein the term viscosity refers to Newtonian viscosity in contrast to the thixotropic viscosity, measured on a Brookfield viscometer. While reducing the viscosity of conventional nail polishes by dilution with a suitable thinner can result in a composition which may flow easily to the non-bristle nib of the present applicator means, such a composition is essentially useless as a nail polish since the pigment and/or other solids content of the nail polish is reduced to a point where it becomes impossible to obtain satisfactory coverage of the nail surface.

Accordingly, the principal objective of the present invention is to provide a novel nail polish composition, suitable for being dispensed via a substantially non-bristle tip affixed to a pen and wherein said nail polish composition substantially eliminates the tendency of the pigment contained therein from separating in the tip or nib of the pen while being dispensed.

These and other objects will be readily apparent from the detailed description of the invention set forth below.

BRIEF DESCRIPTION OF THE DRAWINGS

FIG. 1 is an exploded view of the components of the nail polish applicator.

FIG. 2 is an exploded view of the valve means used in the applicator.

DETAILED DESCRIPTION OF THE INVENTION

The nail polish composition of the present invention is generally prepared by mixing suitable pigment paste or slurry with a final lacquer formulation. While the novel formulations may be prepared without pigments, the compositions generally contain at least one pigment ingredient. The pigment paste or slurry is prepared by grinding a suitable pigment or combination of pigments in a mill base.

Suitable pigments for use in the mill base include all those known and conventionally used in the cosmetic industry, and hence should be non-toxic, non-sensitizing, non-staining, substantially insoluble in solvents, essentially free from a tendency to bleed, compatible with solvents used in the lacquer formulation and moderately stable to light. The average particle size of the selected pigment should be very small, i.e. from about 0.1 microns to about 2.0 microns to insure satisfactory dispersing properties.

As a practical matter, pigments used in nail polish must conform to appropriate national legislation, which in the United States means that the pigment or colorant must be certified by the Food and Drug Administration (FDA). The most widely used pigments include the following: D&C Red 6, D&C Red 30, D&C Red 36, D&C Red 9, D&C Red 7, D&C Red 21, D&C Red 34, FD&C Yellow 5, FD&C Yellow 6, Ferric Ferrocyanide, and cosmetic iron oxides. In addition to the foregoing, titanium dioxide is frequently used as a pigment in combination with other pigments, primarily to impart opacity and to produce pale, finished pigment shades.

Pigments may be ground individually as well as in combination to produce a desired pigment shade. The amount of pigment utilized in the preparation of the paste or slurry ranges from about 20.0% to about 80.0%. Nevertheless, one skilled in the art will recognize that the amount of pigment incorporated into the mill base will depend on the specific properties of the pigment or pigments utilized, e.g. density and oil absorption, as well as the viscosity of the combined mill base and pigment and the processing equipment requirements.

In accordance with the present invention, the pigment (or pigments) selected for use is ground in a mill base formulation to provide a paste composition which may be directly incorporated into a lacquer formulation to provide a finished coating composition, e.g. nail polish.

The essential components of the mill base, into which the pigment is ground, comprise (1) a water-insoluble protective colloid capable of preventing flocculation of the pigment particles and which is compatible with the film former present in the lacquer composition; and (2) a plasticizer, having low volatility and which is both compatible with the protective colloid in the mill base as well as the film former used in the final coating composition. A preferred mill base is one which is essentially non-flammable and non-explosive and which, when combined with the pigment and plasticizer, will provide a composition having a consistency suitable to permit grinding on high shear equipment. The resultant pigment paste composition, i.e. finely ground pigment in combination with the mill base ingredients, should be easily dispersable in a lacquer composition without substantially increasing the viscosity of the finished coating product.

The protective colloid utilized in the mill base should be sufficiently soluble in the plasticizer used therein and the amount of the protective colloid should be adequate to provide enough material to completely coat the dispersed, individual pigment particles with at least a monomolecular layer. Generally, the molecular weight of the colloid should be sufficient to provide an adequate colloidal effect to prevent pigment particles from agglomerating or flocculating. Moreover, the colloid chosen should be compatible with cellulose nitrate or other desired film forming agents present in the lacquer composition.

While the foregoing are the primary criteria for selecting a suitable protective colloid, it is also important that it be soluble in the solvent system used in the finished product and not appreciably increase the viscosity of the finished product, i.e. to a degree which impedes flow through the applicator's non-bristle tip. Other considerations which should be taken into account in selecting a suitable protective colloid include: its stability in the final formulation; its suitability for end use, i.e. innocuous to surfaces to which the finished coating composition is to be applied, e.g. fingernails; its effect on the properties of final coating composition, e.g. gloss, adhesion, resistance to environmental conditions, depth of finish, flexibility and hardness of the film coating.

Representative chemical groups of preferred suitable protective colloids include: saccharide based polymers, acrylic polymers, polyesters, alkyd resins, polyamides, cellulosic polymers, sulfonated naphthalenes, vinyl polymers, formaldehyde condensates, polyurethanes, substituted pyrrolidone polymers, and polypropylene oxides. Preferred protective colloids for use in the mill base of the present invention include toluene sulfonamideformaldehyde condensates (for example Monsanto's SANTOLITE MHP), methyl-butyl methacrylate copolymer (Rohm & Haas' Acryloid B-66") benzoate, ethyl cellulose, dimer acid based polyamide resin (Henkel's Versamide 940) and polymeric esterified pentaerythritol (Hercules' Herco-Flex 900).

Generally, the amount of protective colloid utilized in the mill base is that which is necessary to prevent agglomeration or flocculation of the pigment particles. It has been found that acceptable results are achieved when the protective colloid is present in amounts ranging from about 2.0% to about 80.0% by weight.

The selection of the plasticizer component used in the mill base of the present invention should be based on the following general criteria: its low volatility; its ability to sufficiently solubilize the chosen protective colloid; its compatibility with the chosen film former and other ingredients in the lacquer formulation for the finished product; its ability not to appreciably increase the viscosity of the finished product; its suitability for the desired end use, i.e. dermatologically innocuous; and its ability to impart desirable properties to the finished product, e.g. flexibility and adhesion, color fastness and stability.

Within these general parameters, those skilled in the art will readily recognize suitable plasticizers among the following chemical groups: abietic acid derivatives, acetic acid derivatives, adipic acid derivatives, azelaic acid derivatives, benzoic acid derivatives, polyphenyl derivatives, citric acid derivatives, epoxy derivatives, proprietary esters, ether derivatives, formal derivatives, glutaric acid derivatives, glycerol derivatives, glycol derivatives, linear dibasic acid derivatives, petroleum derivatives, isobutyric acid derivatives, isophthalic acid derivatives, lauric acid derivatives, mellitates, myristic acid derivatives, nitrile derivatives, oleic acid derivatives, palmitic acid derivatives, paraffin derivatives, pelargonic acid derivatives, pentaerythritol derivatives, phosphoric acid derivatives, phthalic acid derivatives, polyesters, ricinoleic acid derivatives, sebacic acid derivatives, stearic acid derivatives, styrene derivatives, sucrose derivatives, sulfonic acid derivatives, terephthalic acid derivatives, tartaric acid derivatives, carbonic acid derivatives, aconitic acid derivatives, maleic acid derivatives, fumaric acid derivatives as well as camphor and castor oil.

Preferred plasticizers include N-ethyl toluene sulfonamide (Santicizer 8), butyl benzyl phthalate (Santicizer S160), alkyl sulphonic esters of phenol e.g. "Mesamoll" (Mobay Chemical Co.), tricresyl phosphate, and dibutyl phthalate.

While the amount of plasticizer utilized in the mill base should be sufficient to solubilize the protective colloid, it generally has been found that an amount ranging from about 20% to about 98% by weight is effective.

Surfactants may be optionally included in the mill base to aid pigment dispersion. When present, the amount of surfactant depends on the specific surfactant(s) used and properties desired; however, it has been found that the amount of surfactant(s) may range from about 0.1% to about 5.0%. While any surfactant compatible with the ingredients in the finished composition may be utilized, Nalco 2395 or Troykyd Solvent Anticrater 366 has been found to produce acceptable results.

The combined pigment and preferred mill base composition can be processed (milled) under high-shear conditions to provide a pigment paste composition wherein the average particle size of the pigment is in the range of about 0.1 microns to about 2.0 microns.

The preferred pigment composition has a paste-like consistency which may be directly mixed with a suitable lacquer formulation. However, as a practical matter, the pigment paste is generally first combined with the appropriate lacquer thinner and thereafter, the remaining ingredients are added.

The following Examples are illustrative of procedures which have been found useful for the preparation of specific mill bases and pigment compositions made in accordance with the present invention.

EXAMPLE 1

A two hundred pound batch of mill base was prepared in accordance with the following procedure. 159 lbs. (79.5% by weight) of plasticizer, (Santicizer 8), i.e., N-ethyl toluene sulfonamide was weighed out on a Toledo floor scale and poured into a steam-jacketed kettle equipped with a "Lightnin" variable-speed, propeller mixer. The plasticizer was heated to a temperature of 190° F. while being stirred. 41 lbs. (20.5% by weight) of protective colloid (Santolite MHP), i.e., toluene sulfonamideformaldehyde condensate was weighed out on a Toledo floor scale and broken into small pieces, the approximate diameters of which were no greater than about 1". The mixer speed was then increased to a point just prior to splashing and the protective colloid was slowly added to the plasticizer, the temperature of which was maintained at 170° F. until all of the protective colloid was dissolved. Thereafter, the mixture was cooled to and maintained at a temperature of between 120° to 140° F.

EXAMPLE 2

The procedure of Example 1 is repeated in the preparation of 50 lb. batches of each of the following mill base formulations:

| Ingredients | |
|---|---|
| (A) Santicizer 160 | 95.0% by weight |
| Acryloid B66 (Rohm & Haas) | 5.0% by weight |
| (B) Santicizer 8 | 97.0% by weight |
| Versamide 940 (Henkel Chemicals) | 3.0% by weight |
| (C) Santicizer 8 | 85.0% by weight |
| Sucrose Benzoate (Velsicol Prod.) | 15.0% by weight |
| (D) Tricresyl Phosphate (Monsanto) | 96.0% by weight |
| Ethyl Cellulose (Hercules Chemicals) | 4.0% by weight |
| (E) Tricresyl Phosphate (Monsanto) | 93.0% by weight |
| Herco Flex 900 Polyester (Hercules Chem.) | 7.0% by weight |
| (F) "Mesamoll" (Mobay Chemical Co.) | 80.0% by weight |
| Santolite MHP | 20.0% by weight |
| (G) Dibutyl phthalate | 50.0% by weight |
| Santolite MHP | 50.0% by weight |

The following general procedure was used in preparing the pigment paste compositions of Examples 3–13.

EXAMPLE 3

An amount of mill base, prepared in accordance with Example 1, is placed into a change-can-paste mixer, the temperature of the mill base being between 120° F. to 140° F. A desired pigment shade is determined and appropriate amounts of an individual pigment or pigment mixture is weighed out and hand stirred into the mill base to prevent excessive dusting. The change-can, containing the pigment and mill base is placed under the mixer and mixed until a well dispersed slurry, completely free of lumps or dry pigment, is obtained. The milling equipment, i.e. a Buehler SDX-600 three-roll mill having standardized roller speeds, is prepared for operation by preheating the rolls to temperatures ranging from about 72° F. to about 124° F.; setting the hydraulic pressure of the rolls in a range from about 15 to 18.5 Bars (about 220 lbs. to about 272 lbs); and setting the hydraulic pressure of the knife at 7 Bars (about 103 lbs.). The slurry in the change can is then transferred to the mill and milled by passing the material through the mill a sufficient number of times at the specific parameters necessary to obtain a paste having the desired average pigment particle size, i.e. from about 0.1 to about 2.0 microns. Slurry material which does not pass through the mill rolls, i.e. "hang-back" material, is moistened with additional amounts of the slurry sufficient to enable it to pass through the rolls. Thereafter, the milled pigment paste is transferred to a clean change-can paste mixer and mixed until uniform.

EXAMPLE 4

In accordance with the procedure of Example 3, a 2300 gram batch of a pigment paste composition was prepared using:

| | |
|---|---|
| Mill Base (Example 1) | 62.5 by weight |
| D & C Red #7 Calcium Lake | 37.5 by weight |

The three rolls of the Buehler SDX-600 mill were preheated to 99° F. and then rolls 1 and 3 were cooled to 97°. The hydraulic roll pressure was set at 18.5 Bars (272 lbs.). The hydraulic knife pressure was set at 7 Bars (103 lbs.). The pigment slurry was passed through the mill three times at the above conditions and the resulting pigment paste composition was found to have an average particle size ranging from about 0.1 to about 2.0 microns as measured by Precision's grind gauge (N.I.P.I.R.I. 625½ Mu) having a range of 0–12½ microns.

EXAMPLE 5

In accordance with the procedure of Example 3, a 2300 gram batch of a pigment paste composition was prepared using:

| | |
|---|---|
| Mill Base (Example 1) | 70.0% by weight |
| D & C Red #7 Rosinated Ca. Lake | 30.0% by weight |

The three rolls of the Buehler SDX-600 mill were preheated to 106° F. and then rolls 1 and 3 were cooled to 97° F. The hydraulic roll pressure was set at 18.5 Bars (272 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by grind gauge used in Example 4.

EXAMPLE 6

The procedure of Example 3 was repeated in preparing a 2300 gram batch of a pigment paste composition using:

| | |
|---|---|
| Mill Base (Example 1) | 70.0% by weight |
| D & C Yellow #5 Zirconium Lake | 30.0% by weight |

The three rolls of the Buehler SDX-600 mill were preheated to 99° F. and then rolls 1 and 3 were cooled to 90° F. The hydraulic roll pressure was set at 16.5 Bars (243 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 7

The procedure of Example 3 was repeated in preparing a 2300 gram batch of a pigment paste composition using:

| | |
|---|---|
| Mill Base (Example 2G) | 48.520% by weight |
| Cosmetic Ferric Ferrocyanide | .200% by weight |
| D & C Red #6 Ba. Lake | 1.729% by weight |
| D & C TiO$_2$ | 44.969% by weight |
| Cosmetic Iron Oxide M | 3.216% by weight |
| D & C Yellow #5 Zr. Lake | 1.366% by weight |

The three rolls of the Buehler SDX-600 mill were preheated to 127° F. and then rolls 1 and 3 were cooled to 118° F. The hydraulic roll pressure was set at 18.5 Bars (272 lbs.). The hydraulic knife pressure was set at 7 Bars (103 lbs.). The pigment slurry was passed three times through the mill at the above conditions and the resulting paste size ranging from about 0.1 to about 2.0 microns as measured by the grind gauge used in Example 4.

EXAMPLE 8

The procedure of Example 3 is repeated in the preparation of a 1000 gram batch of a pigment paste composition using:

| Mill Base (Example 2A) | 62.5% by weight |
| D & C Red #7 Ca. Lake | 37.5% by weight |

The three rolls of a Buehler SDX-600 mill are preheated to 99° F. and the rolls 1 and 3 are cooled to 97° F. The hydraulic pressure is set at 18.5 Bars (272 lbs.). The hydraulic knife pressure is set at 7 Bars (103 lbs.). The pigment slurry is passed three times through the mill at the above conditions to obtain a pigment paste composition having an average pigment particle size ranging from about 0.1 to about 2.0 microns as measured by the grind gauge in Example 4.

EXAMPLE 9

The procedure of Example 3 is repeated in the preparation of a 1000 gram batch of a pigment paste composition using:

| Mill Base (Example 2D) | 70.0% by weight |
| D & C Yellow #5 Zr. Lake | 30.0% by weight |

The three rolls of a Buehler SDX-600 mill are preheated to 99° F. and then rolls 1 and 3 are cooled to 90° F. The hydraulic roll pressure is set at 16.5 Bars (243 lbs.). The hydraulic knife pressure is set at 7 Bars (103 lbs.). The pigment slurry is passed three times through the mill at the above conditions to obtain a pigment paste composition having an average pigment particle size ranging from about 0.1 to about 2.0 microns as measured by the grind gauge in Example 4.

EXAMPLE 10

The procedure of Example 3 was repeated in preparing a 2300 gram batch of a pigment (shade) paste composition using:

| Mill Base (Example 1) | 55.0% by weight |
| D & C Red #6 Ba. Lake | 45.0% by weight |

The three rolls of the Buehler SDX-600 mill were preheated to 106° F. and then rolls 1 and 3 were cooled to 97° F. The hydraulic roll pressure was set at 18.5 Bars (272 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

EXAMPLE 11

The procedure of Example 3 was repeated in preparing a 2300 gram batch of a pigment (shade) paste composition using:

| Mill Base (Example 1) | 70.0% by weight |
| D & C Yellow #6 Al Lake | 30.0% by weight |

The three rolls of the Buehler SDX-600 mill were preheated to 99° F. and then rolls 1 and 3 were cooled to 90° F. The hydraulic roll pressure was set at 15 Bars (220 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge in Example 4.

EXAMPLE 12

The procedure of Example 3 was repeated in preparing a 2300 gram batch of a pigment (shade) paste composition using:

| Mill Base (Example 1) | 69.879% by weight |
| D & C $TiO_2$ | 1.408% by weight |
| D & C Red #34 Ca. Lake | 26.924% by weight |
| Cosmetic Ferric Ferrocyanide | 1.789% by weight |

The three rolls of the Buehler SDX-600 mill were preheated to 99° F. and then rolls 1 and 3 were cooled to 90° F. The hydraulic roll pressure was set at 16.5 Bars (243 lbs.). The hydraulic knife pressure was set at 7 Bars (103 lbs.). The pigment slurry was passed three times through the mill at the above conditions and the resulting paste composition was found to have an average pigment particle size ranging from about 0.1 to about 2.0 microns as measured by the grind gauge used in Example 4.

It should be clear, from the foregoing, that the pigment composition is an intermediate product, ultimately to be incorporated into a lacquer formulation for a nail polish composition.

While the foregoing disclosure and Examples are all directed to the use of a preferred mill base as a grinding medium for various pigment materials to form a pigment paste composition which may be directly incorporated into the lacquer formulation of the present invention, the pigment materials may also be ground in a nitrocellulose containing mill base to form pigment chips in accordance with the conventional "chipping" technology. However, in accordance with the present invention, if a nitrocellulose pigment chip is to be used, it is critical that the viscosity of the final nail polish composition containing the nitrocellulose prepared pigment ingredient(s) not be greater the 200 cps. This can be accomplished by using, for example, a grade of nitrocellulose of about 100 cps nitrocellulose 70% I.P.A. wet in the mill base to form the pigment chip. It is understood that conventional nail polish compositions generally utilize nitrocellulose having a grade not less than approximately 90-100 cps, i.e. ¼ sec nitrocellulose. It is also to be understood that a nail polish pigment chip formulation may be prepared using a grade of nitrocellulose having a viscosity of less than 90 cps, for example 18–25 cps. Using this grade of nitrocellulose will allow a greater pigment load than could be achieved with the nitrocellulose of a grade 90–100 cps. Of course if nitrocellulose chips of the type described above are to be utilized it is necessary to dissolve the color chips in an appropriate solvent to form a pigment dispersion or slurry (shade paste) which thereafter can be mixed with a suitable lacquer formulation to provide a final nail polish composition.

The lacquer formulation of the present invention, in which the pigment paste or slurry is mixed comprises a suitable film forming agent, a copolymer of a hydrophilic and hydrophobic monomer as disclosed hereinbelow and various optional ingredients including: one or more modifying resins, thinners, solvents, diluents, surfactants, flocculating agents or suspending agents.

A preferred film former is 18–25 cps cellulose nitrate. However, it is to be understood that any nitrocellulose polymer may be utilized provided that the viscosity of the final nail polish composition is not greater than 200 cps. Other suitable film formers include: cellulose propionate, cellulose acetate butyrate, ethyl cellulose, sucrose acetate isobutyrate, vinyl polymers, e.g. polyvinyl acetate and polyvinyl alcohol, acrylic resins, e.g. acrylic polymers (thermoplastic acrylic esters, homopolymers and copolymers of alkyl acrylates and methacrylates), urethane polymers, nylon, polyesters and alkyds. Those skilled in the art will appreciate that various other ingredients present in either the lacquer formulation or the final composition may also act as film formers, e.g. the protective colloid used in the mill base, an amount of which will be carried into the final nail polish as part of the pigment paste.

It has been found that the amount of the nitrocellulose film forming agent present in the lacquer formulation generally ranges from about 2.0% to about 20.0%. The amount of preferred nitrocellulose film former, i.e., 18–25 cps generally range from about 3.0% to 15.5% with the preferred range being from about 5.0% to about 10.0% by weight. When film forming agents other than nitrocellulose are used, the amounts present in the polish composition may range from about 2.0% to about 40.0%. It will, of course, be understood by those skilled in the art that in selecting a suitable film forming agent, it will be necessary to strike a balance between the need for building the solids content of the composition, i.e. by way of the film forming agent, but at the same time, insuring that the viscosity of the final composition does not exceed about 200 cps.

It has also been found that copolymers of hydrophobic and hydrophilic monomers impart to the nail polish compositions of the present invention the ability to substantially prevent the pigment or pigments present therein from separating in the nib of the aforementioned pen applicator. Said copolymers are obtained by polymerizing hydrophobic and hydrophilic monomers in a suitable solvent or carrier.

Suitable hydrophobic monomers comprise esters of α-β unsaturated carboxylic acids and alcohols of the formula:

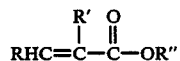

wherein R may be H; CH$_3$; C$_2$H$_5$; R' may be H; CH$_3$ to C$_4$H$_9$; and R''p0 may be:
(i) CH$_3$ to C$_4$H$_9$ straight chain alcohols;
(ii) saturated or unsaturated cyclic alcohols containing up to 20 carbon atoms;
(iii) C$_3$H$_7$ to C$_{16}$H$_{37}$ branched alkyl or C$_5$H$_{11}$ to C$_{22}$H$_{45}$ straight chain alkyl alcohols; and
(iv) alkoxy or aryloxy alkyl alcohols.

The hydrophobic monomers useful in forming the copolymers further comprise a carefully balanced mixture of each of the four classes of esters described above. The hydrophobic monomers may comprise, for example, mixtures formed with from:
(i) about 5 to about 48%, by weight, straight chain alcohols;
(ii) about 5 to about 60%, by weight, saturated or unsaturated cyclic alcohols;
(iii) about 1 to 25%, by weight, branched alkyl or straight chain higher alkyl alcohols; and
(iv) about 1 to about 30% alkoxy or aryloxy alkyl alcohols.

Especially preferred mixtures of the hydrophobic monomers, comprising from:
(i) about 30%, by weight, straight chain alcohols;
(ii) about 40%, by weight, saturated or unsaturated cyclic alcohols;
(iii) about 15%, by weight, branched alkyl or straight chain higher alkyl alcohols; and
(iv) about 10%, by weight, alkoxy or aryloxy alcohols.

The esters formed with the straight chain alcohols defined about which are useful as hydrophobic monomers include methyl acrylate, methyl methacrylate, ethyl acrylate, ethyl methacrylate, propyl acrylate, propyl methacrylate, butyl acrylate or butyl methacrylate. Esters formed with saturated or unsaturated cyclic alcohols described above which are useful as hydrophobic monomers include cyclohexyl acrylate, cyclohexyl methacrylate, benzyl acrylate, benzyl methacrylate, isobornyl acrylate, isobornyl methacrylate, adamantyl acrylate, adamantyl methacrylate, furfuryl acrylate and furfuryl methacrylate. Esters of branched alkyl or straight chain higher alkyl alcohols described above which are useful as hydrophobic monomers include 2-ethylhexyl acrylate, 2-ethylhexyl methacrylate, isobutyl acrylate, isobutyl methacrylate, isooctyl acrylate, isooctyl methacrylate, dodecylacrylate, dodecyl methacrylate, octadodecyl acrylate and octadodecyl methacrylate. Esters of alkoxy or aryloxy alkyl alcohols useful as hydrophobic monomers include methoxyethyl acrylate, methoxyethyl methacrylate, ethoxyethyl acrylate, ethoxyethyl methacrylate, propoxyethyl acrylate, propoxyethyl methacrylate, butoxyethyl acrylate, butoxyethyl methacrylate, phenoxyethyl acrylate, and phenoxyethyl methacrylate.

While it is preferred that the hydrophobic monomers useful in forming the copolymers be comprised of a mixture of each of the four classes of esters described above, it will be appreciated that the hydrophobic monomer portion of the copolymers may be comprised of a mixture of any two or more of the four classes of esters. When the monomers comprising the hydrophobic portion consist of monomers from less than each of the four classes of esters described above, it is generally preferred that monomers from either of classes (i) or (ii) be present in the hydrophobic monomer portion.

Hydrophilic monomers are copolymerized with the hydrophobic monomers described above in forming the copolymers. Suitable hydrophilic monomers include (i) N-substituted acrylamides or methacrylamides, (ii) α-β unsaturated carboxylic acids, and (iii) hydroxyl alkyl acrylates and methacrylates and their homologs. N-substituted acrylamides or methacrylamides useful as hydrophilic monomers include diacetone acrylamide and its homologs as described in U.S. Pat. No. 3,277,056, dimethyl acrylamide, butyl acrylamide, octyl acrylamide, and isobutyl methyl acrylamide.

The α-β unsaturated carboxylic acid hydrophilic monomers include acrylic acid, methacrylic acid, crotonic acid, itaconic acid, maleic acid and fumaric acid.

The hydroxyalkyl acrylate and methacrylate hydrophilic monomers and their homologs include hydroxyethyl acrylate and methacrylate, diethylene glycol monoacrylate and monomethacrylate, triethylene glycol monoacrylate and monomethacrylate, tetraethylene glycol monoacrylate and monomethacrylate, polyethylene glycol monoacrylate and monomethacrylate of molecular weight up to 1000, linear or branched hydroxypropyl acrylate and methacrylate, dipropylene glycol monoacrylate and monomethacrylate, tripropylene glycol monoacrylate and monomethacrylate, tetrapropylene glycol monoacrylate and monomethacrylate, and polypropylene glycol monoacrylate and monomethacrylate of molecular weight up to 1000.

The hydrophilic monomers useful in forming said copolymers may also comprise mixtures of from about 50 to about 75%, preferably about 60 to about 65%, by weight, of the acrylamides described above and from about 25 to about 50%, preferably about 35 to about 40%, by weight, of the α-β unsaturated carboxylic acids described above. Hydroxyalkyl acrylates and methacrylates and their homologs may be included in a ratio of 1:1 with the other hydrophilic monomers described herein.

Preferably, the copolymers are formulated so that the hydrophobic monomers comprise a major portion of the copolymer, for example, the copolymer comprises from about 70 to about 99% hydrophobic monomers, and from about 0.5% to about 30% hydrophilic monomers, said percentages being by weight, based on the weight of the copolymer compositions excluding carrier.

Suitable solvents or carrier in which said hydrophobic and hydrophilic monomers may be polymerized include ethyl acetate, amyl acetate, butyl acetate, butyl cellosolve acetate, cellosolve acetate, methyl cellosolve acetate, acetone, methyl ethyl ketone, methyl isobutyl ketone, butyl cellosolve, cellosolve, methyl cellosolve, ethyl alcohol, isopropyl alcohol, butyl alcohol, toluene, and xylene. Other solvents may also be used as carriers as will be appreciated by those skilled in the art. Suitable carriers may also include any one or a mixture of any of the foregoing solvents in any proportion. A particularly preferred carrier is 1:1 mixture of butyl acetate and isopropyl alcohol. It is of course to be understood that the particular copolymer prepared and incorporated into the nail polish composition of the present invention should be compatible with the other essential ingredients in said composition.

Generally, the process for preparing the copolymer involves mixing the hydrophobic and hydrophilic monomers in a suitable solvent-carrier selected from those set forth hereinabove, to form a uniform mixture and inducing polymerization. Polymerization may be induced by conventional initiators such as peroxides and the like, or by irradiation or redox systems. Polymerization usually occurs at temperatures between about 0° to about 120° C., and preferably at the reflux temperature of the solvent carrier.

The time and temperature of polymerization may be varied in accord with techniques well known in the art.

The amount of the hydrophobic and hydrophilic copolymer present in the final nail polish compositions of the present invention may range from about 5.0% to about 50.0% by weight as a solution. A preferred amount of said copolymer present in the novel nail polish formulation ranges from about 5.0% to about 20.0% by weight. A further preferred range of said copolymer present in the novel formulation is from about 8.0% to about 12.0% by weight. Preferred copolymers of the type disclosed hereinabove include "Polytrap 411", "Polytrap 203" and "Polytrap 400" available from Wickhen Products, Inc. The following Examples 13–20 illustrate suitable copolymer formulations.

EXAMPLE 13

A copolymer composition is prepared by mixing the following ingredients in a 3L, three neck round bottom flask equipped with a stirrer, thermometer and condenser, and heating the mixture at the reflux temperature of the solvent from about 2 to about 24 hours.

| Ingredient | % By Weight |
|---|---|
| Diacetone acrylamide | 3.53 |
| Isobornyl methacrylate | 13.54 |
| Ethyl methacrylate | 11.38 |
| Phenoxyethyl methacrylate | 4.17 |
| Methacrylic acid | 2.28 |
| 2-Ethylhexyl methacrylate | 4.93 |
| Butyl acetate | 29.98 |
| Isopropanol | 29.97 |
| Benzoyl peroxide | 0.22 |
| | 100.00 |

EXAMPLE 14

Using the equipment and following the procedure of Example 13, the following ingredients are combined and polymerized.

| Ingredient | % By Weight |
|---|---|
| Diacetone acrylamide | 3.69 |
| Isobornyl methacrylate | 14.73 |
| Methyl methacrylate | 11.99 |
| Phenoxyethyl acrylate | 2.74 |
| 2-Ethylhexyl methacrylate | 6.91 |
| Methacrylic acid | 1.86 |
| Tetrahydrofurfuryl methacrylate | 0.10 |
| Butyl acetate | 57.75 |
| Benzoyl peroxide | 0.23 |
| | 100.00 |

EXAMPLE 15

A copolymer composition is prepared by mixing the following ingredients in a 0.5 L pressure bottle and heating the mixture at about 90° C. for about 24 hours with constant agitation.

| Ingredient | % By Weight |
|---|---|
| Diacetone acrylamide | 1.77 |
| Dimethyl acrylamide | 1.77 |
| Ethyl methacrylate | 10.62 |
| Cyclohexyl methacrylate | 14.16 |
| Phenoxyethyl methacrylate | 3.54 |
| Methacrylic acid | 1.77 |
| Tetrahydrofurfuryl methacrylate | 0.08 |

| Ingredient | % By Weight |
|---|---|
| Butyl acetate | 32.69 |
| Isopropanol | 32.69 |
| Benzoyl peroxide | 0.91 |
| | 100.00 |

EXAMPLE 16

Using the equipment and following the procedure of Example 15, the following ingredients are combined and polymerized.

| Ingredient | % By Weight |
|---|---|
| Diacetone acrylamide | 1.77 |
| Dimethyl acrylamide | 1.77 |
| Butyl methacrylate | 10.62 |
| Cyclohexyl methacrylate | 14.16 |
| Phenoxyethyl methacrylate | 3.54 |
| Methacrylic acid | 1.77 |
| Tetrahydrofurfuryl methacrylate | 0.08 |
| Butyl acetate | 32.69 |
| Isopropanol | 32.68 |
| Benzoyl peroxide | 0.92 |
| | 100.00 |

EXAMPLE 17

Using the equipment and following the procedure of Example 15, the following ingredients are combined and polymerized at a temperature of about 80° C.

| Ingredient | % By Weight |
|---|---|
| Diacetone acrylamide | 3.48 |
| Hydroxyethyl methacrylate | 3.48 |
| Cyclohexyl methacrylate | 14.59 |
| Ethyl methacrylate | 6.95 |
| Isodecyl methacrylate | 3.48 |
| Methacrylic acid | 2.78 |
| Butyl acetate | 32.27 |
| Ethyl acetate | 32.27 |
| Benzoyl peroxide | 0.70 |
| | 100.00 |

EXAMPLE 18

Using the equipment and following the procedure of Example 15, the following ingredients are combined and polymerized at a temperature of about 120° C.

| Ingredient | % By Weight |
|---|---|
| N—(iso-butoxymethyl) acrylamide | 3.52 |
| Isobornyl methacrylate | 14.24 |
| Methyl methacrylate | 14.24 |
| Methacrylic acid | 1.76 |
| Tetrahydrofurfuryl methacrylate | 0.07 |
| Butyl acetate | 65.39 |
| t-Butyl peroctoate | 0.78 |
| | 100.00 |

EXAMPLE 19

Using the equipment and following the procedure of Example 15, the following ingredients are combined and polymerized at a temperature of about 120° C.

| Ingredient | % By Weight |
|---|---|
| Diacetone acrylamide | 1.75 |
| Octyl acrylamide | 2.16 |
| Methyl methacrylate | 14.19 |
| Isobornyl methacrylate | 14.19 |
| Methacrylic acid | 1.75 |
| Tetrahydrofurfuryl methacrylate | 0.07 |
| Butyl acetate | 65.11 |
| t-Butyl peroctoate | 0.78 |
| | 100.00 |

EXAMPLE 20

Using the equipment and following the procedure of Example 15, the following ingredients are combined and polymerized at a temperature of about 120° C.

| Ingredient | % By Weight |
|---|---|
| Diacetone acrylamide | 3.52 |
| Methyl methacrylate | 14.24 |
| Methoxyethyl methacrylate | 14.24 |
| Methacrylic acid | 1.76 |
| Tetrahydrofurfuryl methacrylate | 0.07 |
| Butyl acetate | 65.39 |
| t-Butyl peroctoate | 0.78 |
| | 100.00 |

The optional modifying resin or resins present in the lacquer formulation must be compatible with the desired film forming agent. The primary role of a modifying resin is to impart one or more of the following properties to the final composition: improved gloss, improved depth of gloss, improved adhesion, improved film hardness, reduced film shrinkage, improved water resistance and increased solids. Suitable modifying resins include: toluene sulfonamideformaldehyde condensates (Santolite MHP and/or Santolite MS-80); sucrose benzoate; sucrose acetate isobutyrate, copolymeric mixtures thereof, alkyds, polyvinyl acetate, polyesters, acrylics, acrylamides, formaldehyde condensates, nylon, Rosin resins, acetates and cyclohexahones. A preferred resin mixture comprises either or both Santolite MHP and Santolite MS-80 (80.0% solution) and Cellovar CV-160 (80.0% solution in butyl acetate) i.e.. sucrose benzoate/sucrose acetate-isobutyrate copolymer.

The amount of the total modifying resin or mixtures thereof present in the lacquer formulation ranges from 0.0% to about 50.0%, with the preferred range being from about 4.0% to about 13.0%, based on 100% solids. In preferred lacquer formulations, Santolite MHP is present in an amount ranging from about 0.2% to about 8.0%, Santolite MS 80 is present in an amount ranging from about 2.4% to about 5.6% and Cellovar CV160 (80%) is present in an amount ranging from about 1.6% to about 3.2%, all figures based on 100% solids.

Other optional ingredients present in the lacquer formulation include those ingredients well known in the art and conventionally employed in such formulations. Examples of such ingredients include plasticizers, e.g. see the list of plasticizers, supra; solvents; suspension agents, e.g. bentone clay; potentiating compounds which enhance the properties of suspension agents, e.g. malic acid; thinning agents, natural and/or synthetic pearlescent pigments, e.g. guanine, metallic powders and U.V. light stabilizers, e.g., Cyasorb 5411.

When pearlescent pigments are incorporated in a final nail lacquer formulation, it has been found that it is possible to utilize grades of nitrocellulose up to and including ⅛ sec.

Specific examples of acceptable metallic powders include, for example cosmetic grades of leafing aluminum or bronze powder. The amount of said metallic powder(s) generally present in a final nail composition is from about 1.0% to about 17.0% by weight. The amount actually used however depends upon the cosmetic affect desired.

It will be understood, however, that the use of particular ingredients in any specific lacquer formulation, of necessity, will be based upon the specific properties and viscosity sought to be obtained in the final product.

Whether incorporated as part of the lacquer formulation or the final nail polish composition, surfactants and flocculating agents may also be utilized.

Surfactants, while optional, have been found to produce a leveling effect on the polish, when applied to the nail surface, as well as improved wear and flow properties. Suitable surfactants include anionic, cationic, non-ionic or amphoteric surfactants that would otherwise be compatible with the nail polish ingredients. However, it should be understood that if bentone is used as a suspension agent, then an anionic surfactant cannot be used since bentone contains a cationic moeity. Examples of suitable anionic surfactants are well known to those skilled in the art and include compounds within the following classification: The saponification products of fats, sulfated fatty acid esters, sulfated fatty amides, sulfated fatty alcohols, phosphate esters of fatty alcohol, amino caboxylated acids, sulfated rosin and sulfated nonionic type surfactants. Examples of cationic surfactants include aliphatic amines with fatty chains and quarternary ammonium salts. Examples of nonionic surfactants include compounds within the following classifications: polyoxyethylene alkylphenols, polyoxyethylene alcohols, polyoxyethylene esters of fatty acids, polyoxyethylene alkyl amines, polyoxyethylene alkylimides, polyol surfactants, polyalkylene oxide block copolymers, propoxylated surfactants, and fluorinated alkyl esters.

In addition to the foregoing, polymeric dispersants may also be incorporated to aid in leveling the nail polish, to aid as a pigment dispersant or to aid flocculation of the pigments into a soft settle. Said dispersants include, among others, silicone polymers and copolymers, polyamides, polyacrylamides and poly-carboxylic acids. The amount of the surfactant or dispersant ingredients present may range from 0.0% to about 10.0%. In accordance with a preferred formulation of the present invention, at least one surfactant or dispersant compound is incorporated into the formulation in an amount ranging from about 0.01% to about 1.0% by weight. Preferred surfactants include: Ethoxylated Castor Oil, e.g., (Nalco Chemicals, "Nalco 2395"); fluorinated alkyl esters, e.g. "3M's" Fluorad FC430; and Troy Chemical's "Troykyd Anticrater 366".

As mentioned supra, suspending agents, for example bentones are utilized to aid in the suspension of pigments. In the absence of such agents, pigments tend to settle in a dense hard pack. In accordance with the present invention, it has been found that bentones should not be present in their traditional amounts, i.e. from about 0.75% to about 1.2%; but rather, if used, should be present at significantly lower levels, e.g. 0.25%. A preferred bentone suspending agent is Bentone 27 which may be prepared for use in the lacquer formulation by placing thinner (75.0%) in a Cowles dissolver equipped with a covered change-can. The mixer is activated and Bentone 27 chips (25.5% bentone, 18.0% camphor and 57.0% dry cellulose nitrate) are slowly added. These materials are mixed under high shear conditions until the camphor and cellulose nitrate dissolves and the bentone is dispersed.

A further optional ingredient that may be used in accordance with the present invention is a flocculent. When present in the final polish formulation, it has been found to promote the soft settling of the pigments. It should be readily apparent to those skilled in the art, that flocculating agents are entirely alien to conventional nail polishes, since it is a generally desired objective in compounding a commercial grade of nail polish to ensure that the ingredients remain in suspension, hence the use of suspending agents such as bentone, etc. Several of the preferred flocculating agents suitable for use include: Nuosperse 700 and Lipophos 42-6. It has also been found that certain amines or quaternized ammonium compounds may be used, e.g., N,N-Bis(2 hydroxyethyl) alkyl amine and soya dimethyl, ethyl ammonium etho-sulphate, respectively. When present, the amount of the flocculating agent utilized in the nail polish ranges from 0.0% to about 10.0% and preferably from about 0.1% to about 5.0% depending on the specific properties of the flocculant used.

The final nail polish is prepared by mixing a suitable pigment paste or slurry with the desired film former and hydrophobic and hydrophilic copolymer and other lacquer ingredients to provide a polish having a viscosity not greater than 200 cps and wherein the pigment concentration ranges from 0.6% to about 16.0%. When the pigment is incorporated into the final composition in the form of a shade (pigment) paste, the concentration of said shade paste ranges from about 3.0% to about 26.0% by weight. For preparing specific nail polishes those skilled in the art will appreciate that the amounts of the ingredients utilized will depend on the specific ingredients chosen. For example, darker pigments generally require the utilization of a lower concentration than lighter pigments in order to obtain satisfactory coverage properties. This caveat notwithstanding, the following are specific examples of the nail polish formulations of the present invention prepared in accordance with conventional nail polish compounding techniques and procedures, bearing in mind, however, that it has been found that as a first manufacturing step the pigment (shade) paste ingredient is preferably mixed with a suitable thinner and any solid resin that may be used and thereafter the remaining lacquer ingredients.

TABLE 1

| Nail Polish Formulations | | | | |
|---|---|---|---|---|
| | Examples | | | |
| Ingredients | A | B | C | D |
| Nitrocellulose, R.S. 18–25 cps 70%, Isopropanol Wet | 10.0 | 6.0 | 5.0 | 7.0 |
| Toluene | 17.7 | 12.0 | 23.1 | 12.0 |
| n-Butylacetate | 21.1 | 4.7 | 21.1 | 8.7 |
| Ethyl acetate (85–88%) | 4.8 | 4.8 | 5.9 | 5.6 |
| Methyl ethyl Ketone | 10.0 | 21.1 | — | 21.1 |
| Santolite MHP[1] | 4.0 | — | — | 4.0 |
| Santolite MS-80[2] | 5.0 | 5.0 | 3.0 | 5.0 |
| Cellovar CV-160[3] | 3.0 | 3.0 | 3.0 | 3.0 |
| Troykyd 366[4] | 0.1 | 0.1 | 0.1 | 0.1 |
| Nalco 2395[5] | 0.3 | 0.3 | 0.3 | 0.3 |
| Shade Paste[6] | 12.0 | 12.0 | 8.5 | 12.0 |
| Bentone 27 paste[7] | 2.0 | 1.0 | — | 1.2 |
| Copolymer[8] | 10.0 | 30.0 | 15.0 | 20.0 |
| Copolymer[9] | — | — | 15.0 | — |

TABLE 1-continued

| | Nail Polish Formulations | | | |
|---|---|---|---|---|
| | Examples | | | |
| Ingredients | A | B | C | D |
| | 100.00 | 100.00 | 100.00 | 100.00 |

Specific ingredients used in Table 1 are further identified hereinbelow:
[1]Santolite MHP - "Monsanto's" toluene sulfonamide-formaldehyde condensate.
[2]Santolite MS-80 - "Monsanto's" 80% solution toluene sulfonamide-formaldehyde condensate (% in formulations based on 80%).
[3]Cellovar CV-160 - "Cellofilm's" 80% solution sucrose benzoate/sucrose acetate-isobutyrate copolymer (% in formulations based on 80%).
[4]Troykyd 366 - "Troy Chemicals's" surfactant.
[5]Nalco 2395 - "Troy Chemical's" Ethoxylated Castor Oil.
[6]Shade Paste - Example 7 "Pale Lilac".
[7]Bentone 27 paste - Bentone chips 25%; thinner 75%.
[8]Wickhen Products, Inc. "Polytrap 411".
[9]Wickhen Products, Inc. "Polytrap 203".

The viscosity of the nail polish formulations disclosed in Table 1 do not exceed 200 cps. This viscosity parameter is a Newtonian viscosity measured at 25° C. on a Brookfield viscometer Model LVT. Spindle No. 1, turning at 60 rpm, was used to measure the viscosities of polish formulations having a viscosity of less than 100 cps. Spindle No. 2, turning at 60 rpm, was used to measure the viscosities of polish formulations having a viscosity between 100 cps and 200 cps. The viscosity measurements were all taken after vigorously agitating the nail polish composition in order to eliminate any thixotropic viscosity. More specifically, it was found that the formulations A-D all had viscosities less than about 40 cps. While the upper range of the viscosity of the nail polish compositions of the present invention may be as high as about 200 cps, it has been found that in preferred compositions, the viscosity should not exceed about 75 cps and preferably is in the range of from about 20 cps to about 45 cps.

The novel, low viscosity nail polish compositions of the present invention have been formulated for use in conjunction with a pen-like dispensing means for applying polish to the nails. With reference to FIGS. 1 and 2, which depict, respectively, exploded views of the dispensing means and internal valve means, the device comprises a cylindrical sleeve or tube member 11, having a closed end 13 and an open end 15 formed with a projecting cylindrical tip 17 having external threads 19; a substantially cylindrically shaped spring valve assembly 21, adapted to fit snuggly within the open end of sleeve 11, said valve assembly 21 comprising a substantially cylindrical case 23, a spring-biased pin 25 and top hat 27; a substantially cylindrical nib holder 29, the interior of which is formed with internal threads, designed to mate with the external threads 19 of the sleeve 11, said nib holder further comprising a reservoir portion and a cylindrically shaped washer 31 constructed of a porous material; a substantially cylindrically shaped solid nib member 33 constructed of a substantially fibrous material and having a shaped tip portion 35; and a substantially cylindrical cap 37 adapted to cover both the nib 33 and nib holder 29. The novel nail polish of the present invention is contained within the sleeve 10 along with one or more mixing balls (not shown). The valve assembly 21 prevents leakage of the nail polish. Polish is delivered to the nib 33 by depressing the tip 35 of nib 33 against a rigid surface, which causes the distal end of nib 33 to engage and activate the spring-biased pin 25 of valve assembly 21, thereby discharging an amount of polish contained in the sleeve 11 body portion of the device into a reservoir portion of the nib holder. In this manner, the polish contacts both the porous washer within the nib holder and the distal end of the nib and flows to the nib tip.

We claim:

1. A novel, low viscosity nail polish composition comprising from about 2.0% to about 40.0% nitrocellulose primary film former; from about 0.6% to about 16.0% pigment; from about 5.0% to about 50.0% of a copolymer comprising hydrophobic and hydrophilic monomers; and an amount of thinner sufficient to render the Brookfield viscosity of the final composition not greater than about 200 cps.

2. A nail polish composition according to claim 1, wherein the pigment is incorporated in the form of a shade paste comprising 20%-80% pigment in mill base, said composition comprising about 3% to about 26% shade paste.

3. A nail polish composition according to claim 1 wherein the primary film former is nitrocellulose having a grade of less than about 90 cps; said film former being present in an amount ranging from about 2.0% to about 20.0% by weight; and wherein the composition has a viscosity not greater than about 75 cps.

4. A nail polish composition according to claim 3 wherein the primary film former is 18-25 cps nitrocellulose and is present in amounts ranging from about 5.0% to about 10.0% by weight and wherein the composition has a viscosity of less than about 45 cps.

5. A nail polish composition according to claim 1, wherein the copolymer is present in an amount of from about 5.0% to about 20.0%, based on the weight of the composition.

6. A nail polish composition according to claim 1, wherein the hydrophobic monomers in said copolymer comprise a major portion of said copolymer.

7. A nail polish composition according to claim 1, wherein the copolymer comprises from about 70 to about 99.5% hydrophobic monomers, and from about 0.5 to about 30% hydrophilic monomers, by weight, based on the weight of the copolymer.

8. A nail polish composition according to claim 1 wherein the hydrophobic monomers in said copolymer comprise esters of $\alpha$-$\beta$ unsaturated carboxylic acids and alcohols of the formula:

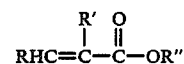

wherein
R may be H; $CH_3$; $C_2H_5$; and
R' may be H; $CH_3$ to $C_4H_9$; and
R" may be:
(i) $CH_3$ to $C_4H_9$ straight chain alcohols;
(ii) saturated or unsaturated cyclic alcohols containing up to 20 carbon atoms;
(iii) $C_3H_7$ to $C_{16}H_{37}$ branched alkyl or $C_5H_{11}$ to $C_{22}H_{45}$ straight chain alkyl alcohols; and
(iv) alkoxy or aryloxy alkyl alcohols.

9. A nail polish composition according to claim 8 wherein the esters comprise a mixture of esters formed with from:
(i) about 5 to about 48%, preferably 35%, by weight, of said straight chain alcohols;
(ii) about 5 to about 60%, preferably about 40%, by weight, of said saturated or unsaturated cyclic alcohols;

(iii) about 1 to 25%, preferably about 15%, by weight, of said branched alkyl or straight chain higher alkyl alcohols; and (iv) about 1 to about 30%. preferably about 10%, by weight, of said alkoxy or aryloxy alkyl alcohols.

10. A nail polish composition according to claim 9, wherein the hydrophobic monomers in said copolymer comprise a mixture of any two or more of the esters of classes (i) and (ii).

11. A nail polish composition according to claim 1 wherein the hydrophilic monomers in said copolymer comprise mixtures of N-substituted acrylamides or methacrylamides and α-β unsaturated carboxylic acids, and hydroxyalkyl acrylates and methacrylates and their homologs.

12. A nail polish composition according to claim 11 wherein the hydrophilic monomers comprise mixtures of from about 50 to about 75%, by weight of said acrylamides and from about 25 to about 50%, by weight, of said α-β unsaturated carboxylic acids.

13. A nail polish composition according to claim 2 wherein the shade paste comprises at least one conventional pigment material and an essentially non-flammable, non-explosive mill base comprising a water insoluble protective colloid compatible with said primary film former and an essentially non-flammable low volatizing plasticizer which is compatible with the primary film former.

14. A nail polish composition according to claim 13 wherein the protective colloid in the mill base is selected from the group consisting of saccaharide based polymers; acrylic polymers; polyesters; alkyd resins; polyamides; cellulosic polymers; sulfonated napthalenes; vinyl polymers; formaldehyde condensates; polyurethanes; substituted pyrrolidone polymers; and polypropylene oxides.

15. A nail polish composition according to claim 14 wherein the protective colloid is selected from the group consisting of toluene sulfonamideformaldehyde condensate; methyl-butyl methacrylate copolymer; sucrose benzoate; ethyl cellulose; polymeric esterified pentaerythritol; and a dimer acid based polyamide resin.

16. A nail polish composition according to claim 15 wherein the amount of the protective colloid present in the mill base ranges from about 2.0% to about 80.0% by weight of the mill base ingredients.

17. A nail polish composition according to claim 13 wherein the plasticizer in the mill base is selected from the group consisting of N-ethyl toluene sulfonamide; butyl benzyl phthalate; an alkyl sulphonic ester of phenol; tricresyl phosphate; and dibutyl phthalate.

18. A nail polish composition according to claim 13 wherein the amount of plasticizer present in the mill base ranges from about 20.0% to about 98.0% by weight of the mill base ingredients.

19. A nail polish composition according to claim 13 wherein the shade paste comprises from about 20.0% to about 80.0% by weight pigment material and from about 20.0% to about 80.0% by weight mill base.

20. A nail polish composition according to claim 2 wherein the shade paste comprises nitrocellulose pigment chips.

21. A nail polish composition according to claim 20 wherein the grade of nitrocellulose is less than about 80 cps.

22. A nail polish composition according to claim 1, further comprising up to about 12% mill base; up to about 50% modifying resins; up to about 10% surfactants' up to about 10% dispersant; and up to about 10% flocculant.

23. A nail polish composition according to claim 22 wherein the modifying resins are present in an amount ranging from about 4.0% to about 13.0%.

24. A nail polish composition according to claim 22 wherein the modifying resins are selected from the group consisting of toluene sulfonamideformaldehye condensates; sucrose benzoate; sucrose acetate isobutyrate, copolymeric mixtures thereof, alkyds, polyvinyl acetate, polyesters, acrylics, acrylamides, formaldehyde condensates, nylon, rosin resins, acetates and cyclohexanones.

25. A nail polish composition according to claim 22 wherein the modifying resins are Santolite MHP, Santolite MS 80 and Cellover-160, said resins being present, respectively, in amounts from about 0.2% to about 8.0% from about 2.4% to about 5.6%, and from about 1.6% to about 3.2%, based on 100% solids.

26. A nail polish composition according to claim 22, wherein the surfactants are selected from the group consisting of anionic, cationic, nonionic or amphoteric surfactants.

27. A nail polish composition according to claim 26, wherein the surfactants are Troykyd Anticrater 366 and Nalco 2395.

28. A nail polish composition according to claim 22 wherein the flocculant is present in amounts ranging from 0.1 to 5.0%.

29. A nail polish composition according to claim 22 wherein the dispersant is Bentone 27.

30. A nail polish composition comprising from about 5.0% to about 10.0% nitrocellulose 18-25 cps; from about 0.2% to about 8.0% Santolite MHP; from about 2.4% to about 5.6% Santolite MS-80; from about 1.6% to about 3.2% Cellovar CV-160; from about 0.01% to about 1.0% Nalco 2395; from about 0.01% to about 1.0% Troykyd 366 Anticrater; 0.6% to about 16.0% pigment; and from about 8.0% to about 12.0% Polytrap 411, said composition having a viscosity not greater than about 200 cps.

* * * * *

UNITED STATES PATENT AND TRADEMARK OFFICE
CERTIFICATE OF CORRECTION

PATENT NO. : 4,747,419
DATED : May 31, 1988
INVENTOR(S) : M. D. Flynn and A. J. Suares It is certified that error appears in the above-identified patent and that said Letters Patent is hereby corrected as shown below:

First page, penultimate line of ABSTRACT, "form" should be --from--;

Col. 3, line 44, before "benzo-" insert --, sucrose--;

Col. 8, line 59, "the" should be --than--;

Col. 9, line 67, after "R" delete "p0";

Col. 10, line 28, "about" should be --above--;

Col. 15, line 25, "moeity" should be --moiety--;

Col. 19, line 4, "30%." should be --30%,--;

line 31, "saccaharide" should be --saccharide--;

Col. 20, lines 13-14, "surfactants'" should be --surfactants;--;

line 29, "Cellover-160" should read --Cellovar-160--; and line 31, after "8.0%" insert a comma.

UNITED STATES PATENT AND TRADEMARK OFFICE
CERTIFICATE OF CORRECTION

PATENT NO. : 4,747,419
DATED : May 31, 1988
INVENTOR(S) : M.D. Flynn and A.J. Suares Page 2 of 2

It is certified that error appears in the above-identified patent and that said Letters Patent is hereby corrected as shown below:

line 31, after "8.0%" insert a comma.

Signed and Sealed this

Third Day of January, 1989

Attest:

DONALD J. QUIGG

Attesting Officer

Commissioner of Patents and Trademarks